(12) United States Patent
Hobo (10) Patent No.: US 6,227,860 B1
(45) Date of Patent: May 8, 2001

(54) DENTAL IMPLANT

(75) Inventor: Sumiya Hobo, Tokyo (JP)

(73) Assignee: Twenty One Inc. (JP)

( * ) Notice: Subject to any disclaimer, the term of this patent is extended or adjusted under 35 U.S.C. 154(b) by 0 days.

(21) Appl. No.: 09/447,618

(22) Filed: Nov. 23, 1999

(30) Foreign Application Priority Data

Nov. 25, 1998 (JP) ................................. 10-333933

(51) Int. Cl.7 .................................................. A61C 8/00
(52) U.S. Cl. .......................................................... 433/173
(58) Field of Search ................................ 433/172, 173, 433/174, 176

(56) References Cited

U.S. PATENT DOCUMENTS

| 2,721,387 | 10/1955 | Ashuckian . |
| 3,708,883 | 1/1973 | Flander . |
| 4,011,602 | * 3/1977 | Rybicki et al. . |
| 4,588,381 | * 5/1986 | Caracciolo ............................ 433/173 |
| 5,087,199 | 2/1992 | Lazarof . |
| 5,209,753 | * 5/1993 | Biedermann et al. ................. 606/72 |
| 5,470,230 | * 11/1995 | Daftary et al. ........................ 433/174 |
| 5,489,210 | * 2/1996 | Hanosh ................................. 433/173 |
| 5,681,167 | * 10/1997 | Lazarof ................................. 433/174 |
| 5,681,187 | 10/1997 | Fukushima et al. . |
| 5,931,674 | * 8/1999 | Hanosh et al. ........................ 433/173 |
| 6,007,337 | * 12/1999 | Bauer ................................... 433/173 |

OTHER PUBLICATIONS

"The Immediate Load Implant System" Quintessence Publishing Co., Ltd., Tokyo, Japan, 1998, Lazarof et al.

* cited by examiner

Primary Examiner—Ralph A. Lewis
(74) Attorney, Agent, or Firm—Ostrolenk, Faber, Gerb & Soffen (57) ABSTRACT

A dental implant that includes a cylindrical body which can be positively secured against micromotion within a bore in a jawbone by a spindle-shaped expansion mechanism and further secured against the contamination by microorganism through a gap in an internal channel of tubular portion by a compressive contact mechanism.

9 Claims, 12 Drawing Sheets

DENTAL IMPLANT

BACKGROUND OF THE INVENTION

1. Field of the Invention

The present invention relates to a dental implant for preparing tooth prosthesis. More specifically, this invention relates to a dental implant having the function for immediate loading after implant placement.

2. Description of the Prior Art

Modern dental implants are designed based upon the biological fact that a titanium-alloy implant and a bone integrate with each other very strongly, bearing a tensile strength more than 100 kg. This fact was found by Branemark of Sweden in 1969, and is called Osseointegration. Typical such osseointegrated implants comprise a tubular body portion called a fixture which is emblaced within a bore drilled in the bone.

Figure 9:
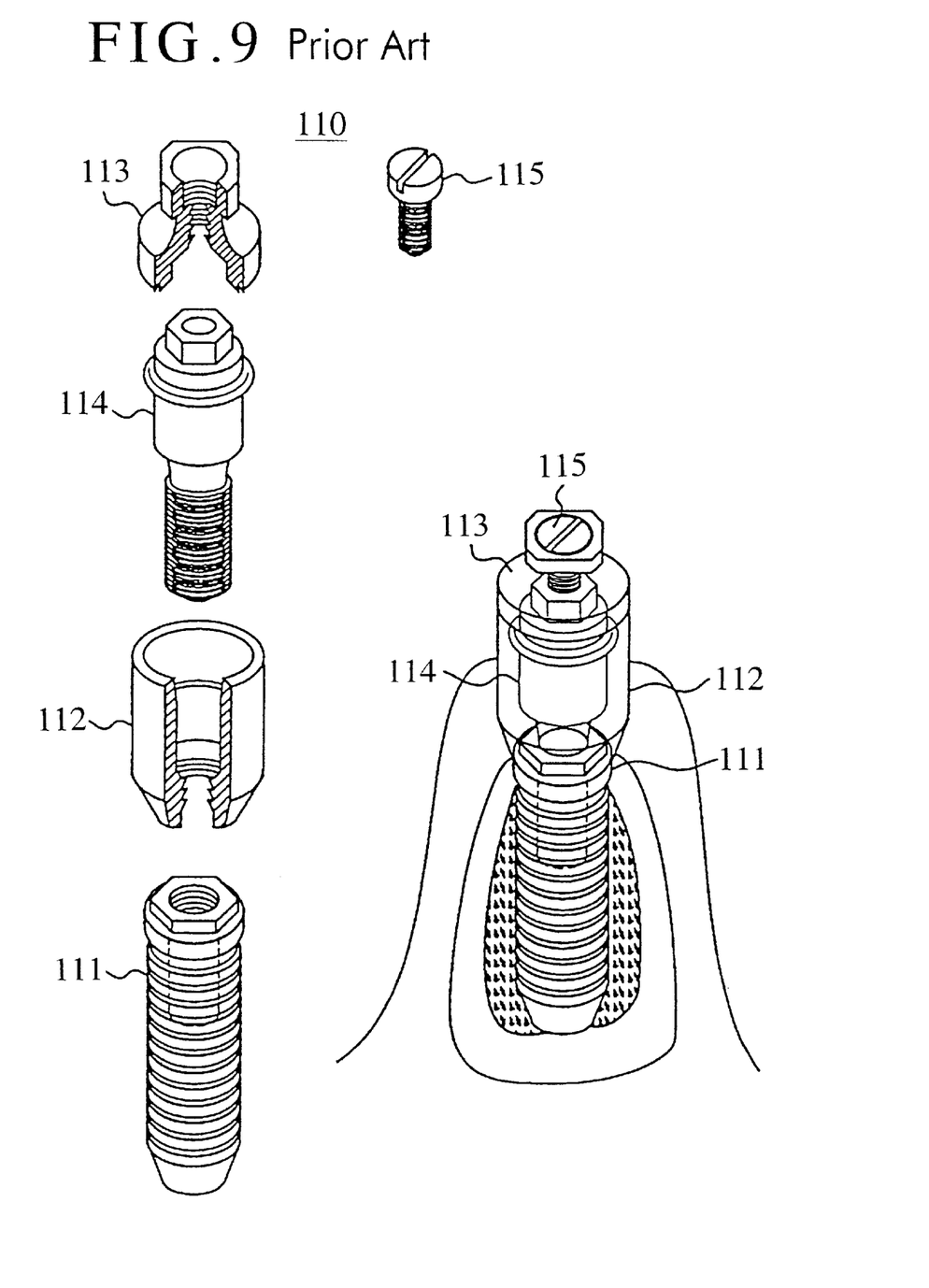
FIG. 9 is a makeup drawing showing an example of dental implant of the prior art.

As shown in FIG. 9, the dental implant 110 developed by Branemark is composed of a fixture 111, an abutment 112, a gold cylinder 113, an abutment screw 114, and a gold screw 115 (totally five pieces). The fixture 111 has a tublar body and is threaded externally, and when implanted in bone it is perfectly osseointegrated with alveolar bone after three to six months. The abutment 112 connects the fixture 111 to the gold cylinder 113 through soft tissue. The gold cylinder 113 connects the abutment 112 to a prosthesis (called an upper structure). The abutment screw 114 fixes the abutment 112 to the fixture 111, and the gold screw 115 fixes the upper structure to the abutment 112 through the gold cylinder 113.

In the method developed by Branemark for using the dental implant 110, it has been ruled out to load by connecting the prosthesis to the implant until three to six months after placing an implant in the alveolar bone under mucous membrane, in order to keep the implant at rest. This is called delayed loading protocol. It was reported that micromotion of the implant was produced by omitting the delayed loading period and when the amount of micromotion exceeded 100 μm, some disorder was caused on the surface between the implant and the bone. On the other hand, in Branemark's method, even solid denture is contraindicated during the delayed loading period of three to six months after implant placement, as its protocol attaches importance for keeping the implant at rest during the period. Since this means to lengthen the necessary period for operation and to bring upon patient's pain, it has been regarded as a problem to be solved.

In order to overcome the drawbacks, it is indispensable to load immediately after implant placement without rest period. Hence, an effective countermeasure to prevent micromobility of the implant becomes necessary. Several types of implants using the mechanical locking means for securing the implant in place within the bore in the jawbone have been suggested. These types of implants have an expansion screw in the internal channel of the fixture, the lower half of the fixture being cut in to the end and divided into several legs, and when the expansion screw is rotated the legs are expanded radially and outwardly, causing the anchoring effect of the fixture in bone. The method to load immediately after implant placement is called immediate loading, and the design to secure the anchoring effect in bone by expanding the legs of the implant in immediate loading is called apical expansion design.

Figure 10:
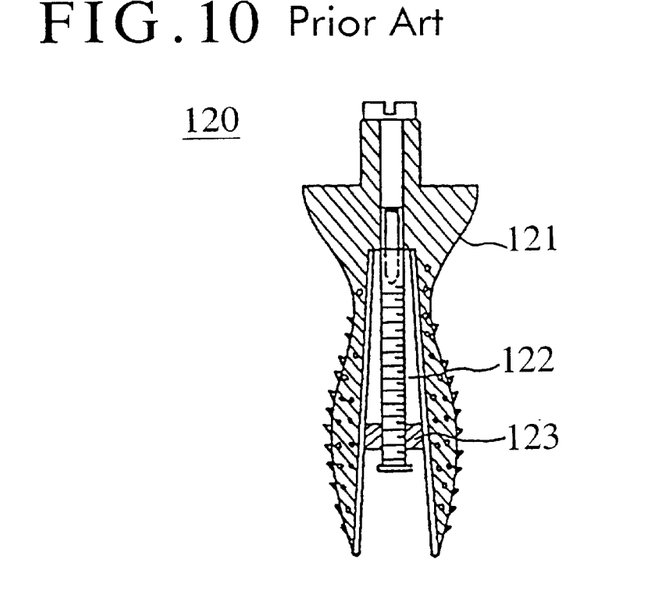
FIG. 10 is an illustrating drawing showing another example of dental implant of apical expansion design of the prior art.

Referring to FIG. 10, the first dental implant 120 of apical expansion design issued in U.S. Pat. No. 2,721,387 to Ashuckian (1955) has spindle-like form imitating the socket of the extracted tooth. In the internal channel of the fixture 121 of the dental implant 120, an expansion screw 122 is inserted. By rotating the expansion screw 122, an expansion nut 123 is drawn upwards, thereby spreading apart two legs which are formed by dividing the lower half of the fixture 121. Thus, the fixture 121 is anchored in bone so as to prevent micromotion of the implant.

Figure 11:
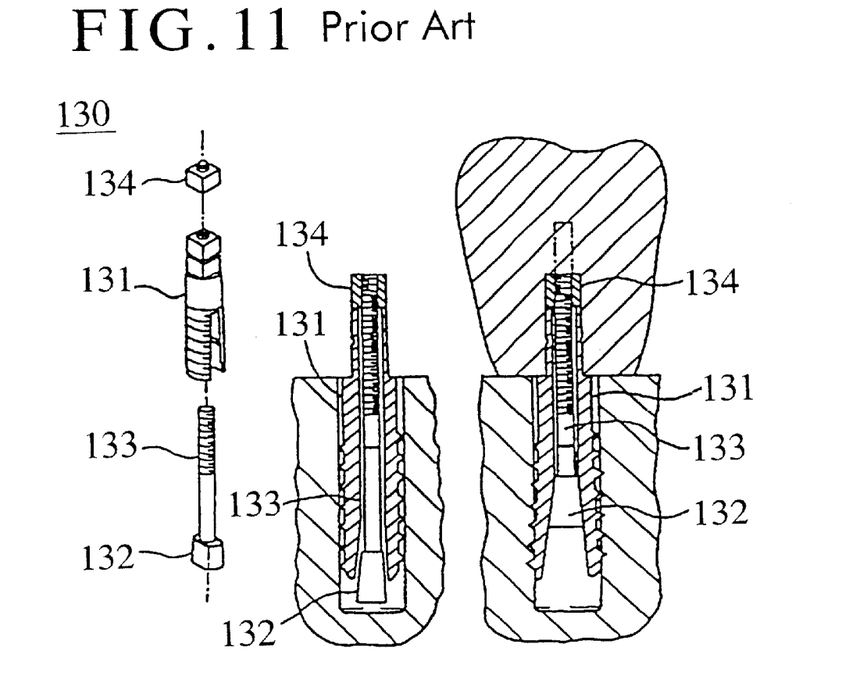
FIG. 11 is an illustrating drawing showing a further example of dental implant of apical expansion design of the prior art.

As shown in FIG. 11, the dental implant 130 of apical expansion design issued in U.S. Pat. No. 3,708,883 to Flander (1973) has the structure that the lower half of a cylindrical fixture 131 is divided into two legs and a frustoconical head 132 is attached on one end of an expansion screw 133 which is inserted into the internal channel of the fixture 131. By rotating a square nut 134 threaded into the other end of the expansion screw 133, the expansion screw 133 is drawn upwards together with the head 132 and the legs of the fixture 131 are expanded.

Figure 12:
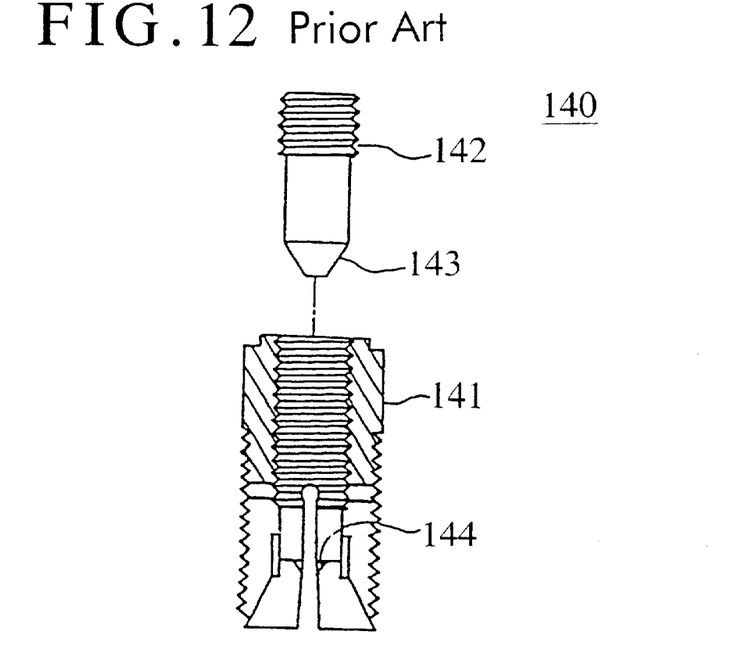
FIG. 12 is an illustrating drawing showing still a further example of dental implant of apical expansion design of the prior art.

As shown in FIG. 12, the dental implant 140 of apical expansion design issued in U.S. Pat. No. 5,087,199 to Lazarof (1992) has the structure that the lower half of a cylindrical fixture 141 is divided into plural legs and an expansion screw 142 having a conical head 143 is inserted into the internal channel of the fixture 141. By rotating the expansion screw 142, the point of the conical head 143 goes down into the hollow 144 at the internal center of the lower portion of the fixture 141, and the legs of the fixture 141 are expanded.

Figure 13:
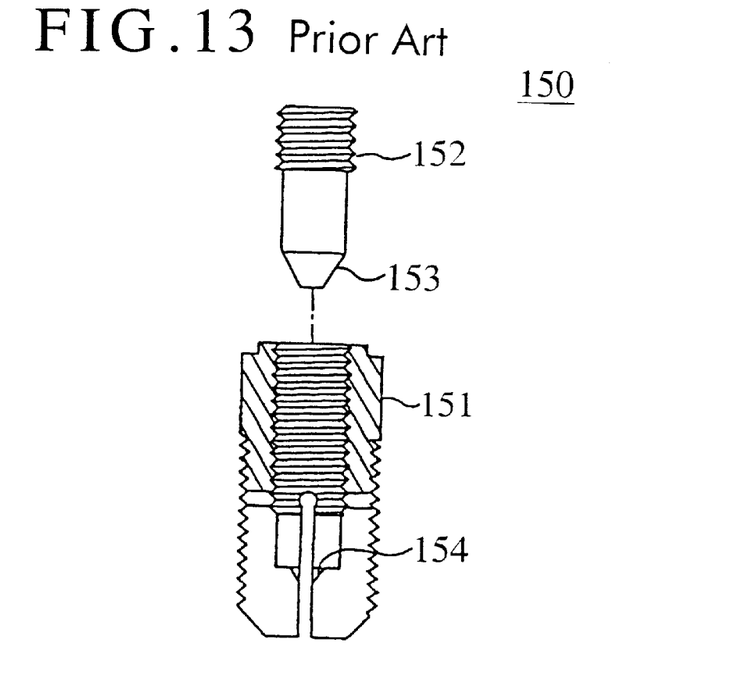
FIG. 13 is an illustrating drawing showing still a further example of dental implant of apical expansion design of the prior art.

Further, as shown in FIG. 13, the dental implant 150 of apical expansion design issued in U.S. Pat. No. 5,489,210 to Hanosh (1996) has the structure resembling closely to the dental implant 140 in that the lower half of a cylindrical fixture 151 is divided into plural legs and an expansion screw 152 having a conical head 153 is inserted into the internal channel of the fixture 151. By rotating the expansion screw 152, the point of the conical head 153 goes down into the hollow 154 at the internal center of the lower portion of the fixture 151, and the legs of the fixture 151 are expanded.

These types of implants of apical expansion design, as described above, have codimon mechanism that they have an expansion screw in the internal channel from the head to the lower end of the cylindrical fixture, the lower half of the fixture being cut in to the end and divided into plural legs, and when th e expansion screw is rotated are expanded radially and outwardly, causing anchoring effect in bone preventing micromotion of the implant.

However, these designs have the risk of micro-leakage of bacteria called microorganisms from the head of the implant exposed in patient's intraoral cavity to the bottom of the implant placed in bone, passing through the micro-gap between the male threads of the expansion screw and the female threads of the internal channel of the fixture. Therefore, the dental implants of these types of apical expansion design may fail unless precautions attention is paid to potential contamination in the apical region, which could cause serious damage to periimplant bone crucial to achieve osseointegration, so that they do not have any practical value.

Figure 14A:
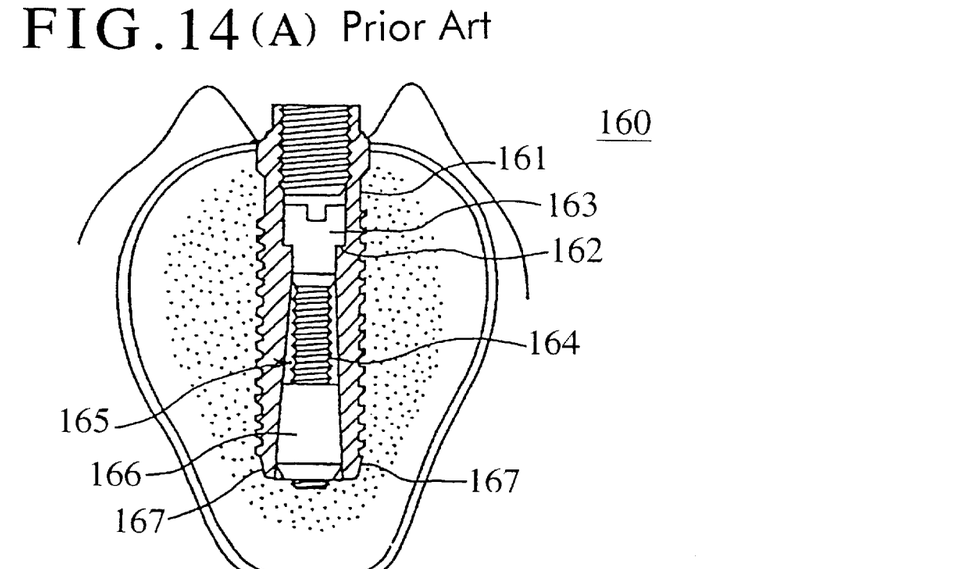
FIG. 14(A) is a sectional view showing still a further example of dental implant of apical expansion design of the prior art before apical expansion.

An improved dental implant 160 of apical expansion design is described in U.S. Pat. No. 5,681,187 issued to Lazarof (1997). The dental implant 160, as shown in FIG. 14(A), has a cylindrical fixture 161, the lower half of which is divided into plural (four) blade-like legs. The fixture 161 has a circular ring-shaped internal shoulder 162 at the upper middle in the internal channel of the fixture 161. A screw head 163, the outer diameter of which is larger than the inner diameter of the internal shoulder 162, and a male screw portion 164 which is inserted through the internal shoulder 162 constitute an expansion screw 165.

Figure 14B:
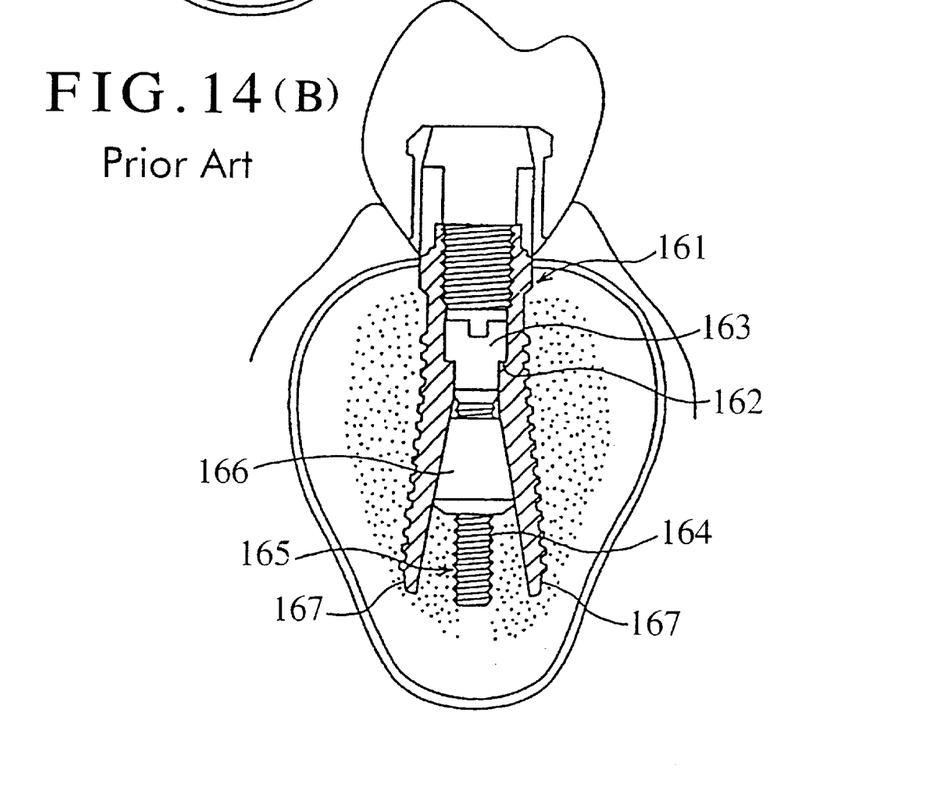
FIG. 14(B) is a sectional view showing that after apical expansion.

When the expansion screw 165 is rotated, a frustoconically-shaped expansion nut 166 is drawn toward the middle of the implant with the result that, as shown in FIG. 14 (B), the legs 167 of the fixture 161 located within the socket of the extracted tooth are spread apart, thereby anchoring the dental implant 160 in bone so as to prevent micromotion.

By means of the structure of the dental implant 160 of apical expansion design described above, when the expansion screw 165 is rotated and the frustoconically-shaped expansion nut is drawn upwards, then the legs 167 of the fixture 161 are expanded and reactive forces to return the legs 167 to their original form work against active forces to expand the legs 167 outwardly. These reactive forces work so as to compress the screw head 163 of the expansion screw 165 to the internal shoulder 162 of the fixture 161, causing a close contact between the both. This is said to be effective for preventing microleakage of bacteria from the head portion of the dental implant 160 to the other end through the internal channel of the fixture 161.

Figure 15:
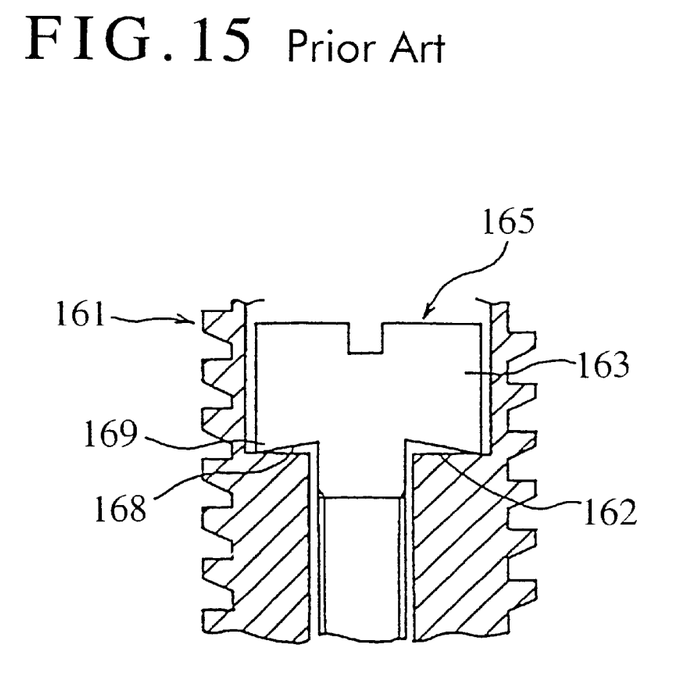
FIG. 15 is a sectional view showing a preventive structure against microorganisms of a dental implant of apical expansion of the prior art.

In the actual product of the dental implant 160, an additional structure is added to reinforce the effect described above (Lazarof S, Hobo S, Nowzari H: "The immediate load implant system", Quintessence Pub. Co., 1988, Tokyo). As shown in FIG. 15, the expansion screw 165 has a 15° reverse bevel 168 on the periphery of the apical side of its crew head 163, forming a circular incisal edge 169. When the expansion screw 165 is tightened to perform apical expansion, the incisal edge 169 of the reverse bevel 168 is compressed in close contact against the upper surface of the internal shoulder 162 of the fixture 161 and deformed by strong compressive force to thereby cause a cold welding effect, so that the passway for micro-leakage of bacteria is sealed. As a result, the effect to prevent microorganisms is reinforced.

However, according to recent clinical experiences, it has become clear that the effect of the dental implant 160 of apical expansion design, shown in FIG. 14, involves the following drawbacks.

As shown in FIG. 14(B), when the expansion screw 165 of the dental implant 160 is rotated and the expansion nut 166 is drawn upwards, the blade-shaped legs 167 formed by dividing the lower half of the fixture 161 are expanded and the points of the blade-shaped legs 167 cut in deep into peripheral bone and fixed. In that case, it cannot be avoided that mechanical stresses are concentrated on the points of the blade-shaped legs 167 and partly damage peripheral bone. Further, in the similar condition, when a strong torque is applied on the head 163 of the dental implant 160, twisting force is produced between the base and the point of each blade-shaped leg 167 of the fixture 161, and the legs 167 sometimes are broken at their bases. Still further, horizontal micromotion of the implant 160 is apt to be produced by a horizontal force applied on the head of the fixture 161 in case that the points of the blade-shaped legs 167 are fixed and the upper body of the fixture 161 is unstable.

On the other hand, during the functioning of the dental implant such as mastification, an occlusal force of 60 kg at maximum is applied downwards on the head 163 of the dental implant 160 exposed in the oral cavity. Since the sum of the cross sectional areas of the threaded shank 164 of the expansion screw 165 and the expansion nut 166 is far larger than that of the legs 167 of the fixture 161, when an occlusal force is applied, the expansion screw 165 and the expansion nut 166 remain at the almost initial position, while the legs 167 of the fixture 161 cut in deep into the bone and move downwards. As a result, the expansion screw 165 moves upwards relative to the fixture 161, making the base of the head 163 of the expansion screw 165 and the upper surface of the internal shoulder 162 of the fixture 161 set apart from each other and destroying the cold welding effect. Consequently, micro-leakage of bacteria through the slight gap between the both is invited. A clinical statistics showed that contamination by microorganisms of the dental implant 160 has been observed with a 3% occurrence rate.

Therefore, to overcome the drawbacks of the dental implant 160 described above, the following problems have to be resolved.

(1) Stresses concentrate on the points of the legs 167 when the legs 167 are expanded, and a twisting force is produced between both ends of each leg 167 when a torque is applied on the head of the fixture 161, while horizontal micromotion of the fixture 161 occurs when a horizontal force is applied on the head of the fixture 161.

(2) Micro-leakage of bacteria occurs when an occlusal force is applied downwards on the head of the implant.

OBJECT OF THE INVENTION

To overcome the drawbacks of the prior art described above, the object of the present invention is to provide a dental implant which has necessary and sufficient features as follows.

1) Mechanical stresses do not concentrate on the points of the legs of the dental implants when the legs are expanded; and any twisting force is not produced between both ends of each leg when a torque is applied on the head of the dental implant, and further horizontal micromotions do not occur when a horizontal force is applied on the head of the dental implant.

2) Micro-leakage of bacteria does not occur when an occlusal force is applied downwards on the head of the dental implant.

SUMMARY OF THE INVENTION

In the present invention, there is provided a dental implant comprising:

a cylindrical body receivable within a bore provided in a jawbone of a patient and having an internal channel from an upper end to an under end of the cylindrical body, including an annular internal shoulder at an upper middle of the internal channel and a skirt portion on an under half of the cylindrical body, plural slits being cut in on the skirt portion so as to form plural blade-like portions in the axis direction of the cylindrical body, female threads being formed on an internal surface of upper portion of the cylindrical body, a nut body including a cylindrical portion inserted into a circular edge of the skirt portion of the cylindrical body and an inner cavity having female threads, a first bolt body including on its upper end a head whose outer diameter is larger than an inner diameter of the internal shoulder of the cylindrical body and including on its under side a shank whose outer diameter is smaller than the inner diameter of the internal shoulder of the cylindrical body, the shank having male threads externally and being engaged with the female threads of the nut body, a connecting body having an internal channel from an upper end to an under end of the connecting body, including an internal shoulder near the under end of the connecting body, the connecting body having an inner diameter smaller than an outer diameter of head of the cylindrical body and larger than an inner diameter of the internal channel of the cylindrical body, the head of the cylindrical body being slided into an under end of the internal channel of the connecting body, head of the connecting body being embodied with a prosthesis, and a second bolt body including a head whose diameter is larger than an inner diameter of the internal shoulder of the connecting body and smaller than an inner diameter of portion of the internal channel of the connecting body positioned above the internal shoulder of the connecting body, and including a shank having male threads externally and having an outer diameter which is smaller than the inner diameter of the internal shoulder of the connecting body, the male threads of the second bolt body being engaged with the female threads provided on the internal surface of upper portion of the cylindrical body, so that inserting the first bolt body into the internal channel of the cylindrical body through the internal shoulder of the cylindrical body and rotating the first bolt body while engaging the male threads of the shank of the first bolt body with the female threads of the nut body causes swelling of the skirt portion of the cylindrical body into a spindle-like shape and causes close contact between a lower surface of the head of the first bolt body and an upper surface of the internal shoulder of the cylindrical body, and so that inserting the second bolt body into the internal channel of the connecting body through the internal shoulder of the connecting body, rotating the second bolt body while engaging the male threads of the shank of the second bolt body with the female threads of the internal channel of the cylindrical body and producing close contact between an under surface of the head of the second bolt body and an upper surface of the internal shoulder of the connecting body causes embodiment of the cylindrical body with a prosthesis through the connecting body.

As apparent from the above, the present invention is not based on the apical expansion design of the prior art, and is based on the spindle-shaped expansion mechanism. By inserting the nut body into the circular edge of the skirt portion of the cylindrical body (hereinafter often referred to as "fixture"), the circular edge of the skirt portion of the fixture is fixed. By rotating the first bolt body fitted into the nut body, its rotating force (torque) is converted to a compressive force applied between both ends of the blade-like portions. In the prior art, the legs of the fixture are expanded by the rotation of the expansion screw. On the other hand, in the present invention, the blade-like portions are swelled into spindle-like shape by rotating the first bolt body (hereinafter occasionally referred to simply as "bolt body") and applying the compressive force in the direction to shorten the distance between both ends of the blade-like portions. This is a remarkable difference between the prior art and the present invention.

In the present invention, the blade-like portions compress peripheral bone by swelling into a spindle-like shape, and its reactive force prevents the micro-motion of the dental implant. At that time, since the compressive force acting on peripheral bone works with the outwardly facing planar abdominal region of the blade-like portions which form a spindle-like shape, the blade-like portions would not cut into bone and mechanical stresses would not be concentrated anywhere. Therefore, the damaging effect on peripheral bone which occurs in the prior art by the concentration of stresses can be avoided. In addition, since the lower ends of the blade-like portions are linked by the circular edge of the skirt portion of the cylindrical body and fixed by the nut body, they constitute a rigid spindle-shaped structure. Therefore, the break-down of blade-like portions at their bases by twisting force does not occur. Finally, since the spindle-like structure is held firmly in peripheral bone as one body, horizontal micromotion can also be avoided.

During the functioning of the dental implant such as mastication, as previously described, an occlusal force of 60 kg at maximum could be loaded downwards on the exposed head of the dental implant in the oral cavity. In the present invention, the stress is applied on the both ends of each blade-like portion in the direction to shorten the length of a string of blade-like portion which is bent like a bow by rotating the bolt body. Comparing under the same strength of occlusal force, the relative displacement of the head of the bolt body to the cylindrical body (fixture) is far smaller in the present invention than in the prior art. As a result, the possibility that the base of the head of the bolt body and the upper surface of the internal shoulder of the fixture are set apart from each other is far smaller in the present invention than in the prior art. Therefore, the preventive effect against the micro-leakage of bacteria through the micro-gap in the internal channel of the fixture is remarkably reinforced in the present invention.

Preferably, the nut body may be furnished with a head having an outer diameter larger than that of the cylindrical portion of the nut body, the nut body having a maximum diameter substantially equal to an outer diameter of the circular edge of the skirt portion of the fixture. Further, the outer diameter of the cylindrical portion of the nut body is slightly larger than an inner diameter of the circular edge of the skirt portion of the fixture, so that the cylindrical portion of the nut body can be pressed into a cavity of the skirt portion of the fixture to thereby enable fixing the nut body to the skirt portion of the fixture.

Since the compressive force is applied in the longitudinal direction of the blade-like portions by tightening the first bolt body and then the blade-like portions could be deformed irregularly, it is preferred that an outward bulge, an inner concave dent or a narrowed portion be formed in the middle of the blade like portions of the fixture. As a result, the blade-like portions can be guided outwardly by the outward bulge, the inner concave dent or the narrowed portion and deformed in an approximately uniform bow-like shape each to thereby swell into a spindle-like shape as a whole.

Preferably, a circular washer composed of a metal softer than the fixture or the first bolt body may be interposed between an upper surface of the internal shoulder of the fixture and a lower surface of the head of the first bolt body so as to cause a cold welding effect on the both surfaces of the circular washer. Thus the passway of bacteria is more effectively sealed to thereby reinforce the preventive effect against microorganisms. It is preferable to use, for example, pure titanium as the metal of the circular washer.

An additional threaded body having male threads on its external surface may preferably be engaged with the female threads provided on the internal surface of upper portion of the fixture, the additional threaded body having a convex jut on its lower surface, the head of the first bolt body having its upper surface furnished with a concave dent which fits closely with the convex jut. By strongly tightening the additional threaded body, the compressive force between the upper surface of the internal shoulder of the fixture and the lower surface of the head of the first bolt body is reinforced, the both being contacted more closely and the contact area of the both being increased more. Thus, the passway of bacteria is more effectively sealed so as to reinforce the preventive effect against microorganisms.

In place of the additional threaded body, preferably, a lower end of the shank of the second bolt body may be roundly pointed, and the length of the shank of the second bolt body may be made so long that the lower end of the shank of the second bolt body reaches and presses strongly an upper surface of the head of the first bolt body when the second bolt body is rotated while engaging the male threads of the shank of the second bolt body with the female threads on the internal surface of the fixture. Thus, a close contact is realized between an under surface of the head of the second bolt body and an upper surface of the internal shoulder of the connecting body. By strongly tightening the second bolt body, the compressive force between the upper surface of the internal shoulder of the fixture and the under surface of the head of the first bolt body is reinforced, the both being contacted more closely and the contact area of the both being increased more. As a result, the passway of bacteria is more effectively sealed so as to reinforce the preventive effect against microorganisms.

Preferably, the lower end of the shank of the second bolt body may be composed of a metal softer than the first bolt body or other part of the second bolt body so as to strengthen the compressive force between the upper surface of the internal shoulder of the fixture and the under surface of the head of the first bolt body. Thus, when strongly tightening the second bolt body, the passway of bacteria is more effectively sealed so as to reinforce the preventive effect against microorganisms. It is preferable to use, for example, pure titanium as the metal of the lower end of the shank of the second bolt body.

BRIEF DESCRIPTION OF THE DRAWINGS

These and other objects and features of the present invention will become clear from the following description taken in conjunction with the preferred embodiments thereof with reference to the accompanying drawings, in which.

DETAILED DESCRIPTION OF THE PREFERRED EMBODIMENT

Preferred embodiments of the present invention will now be described with reference to the attached drawings. Throughout FIGS. 1–15, like parts in view of the function thereof are designated by like numerals to omit repeated description thereof.

The First Preferred Embodiment

Figure 1:
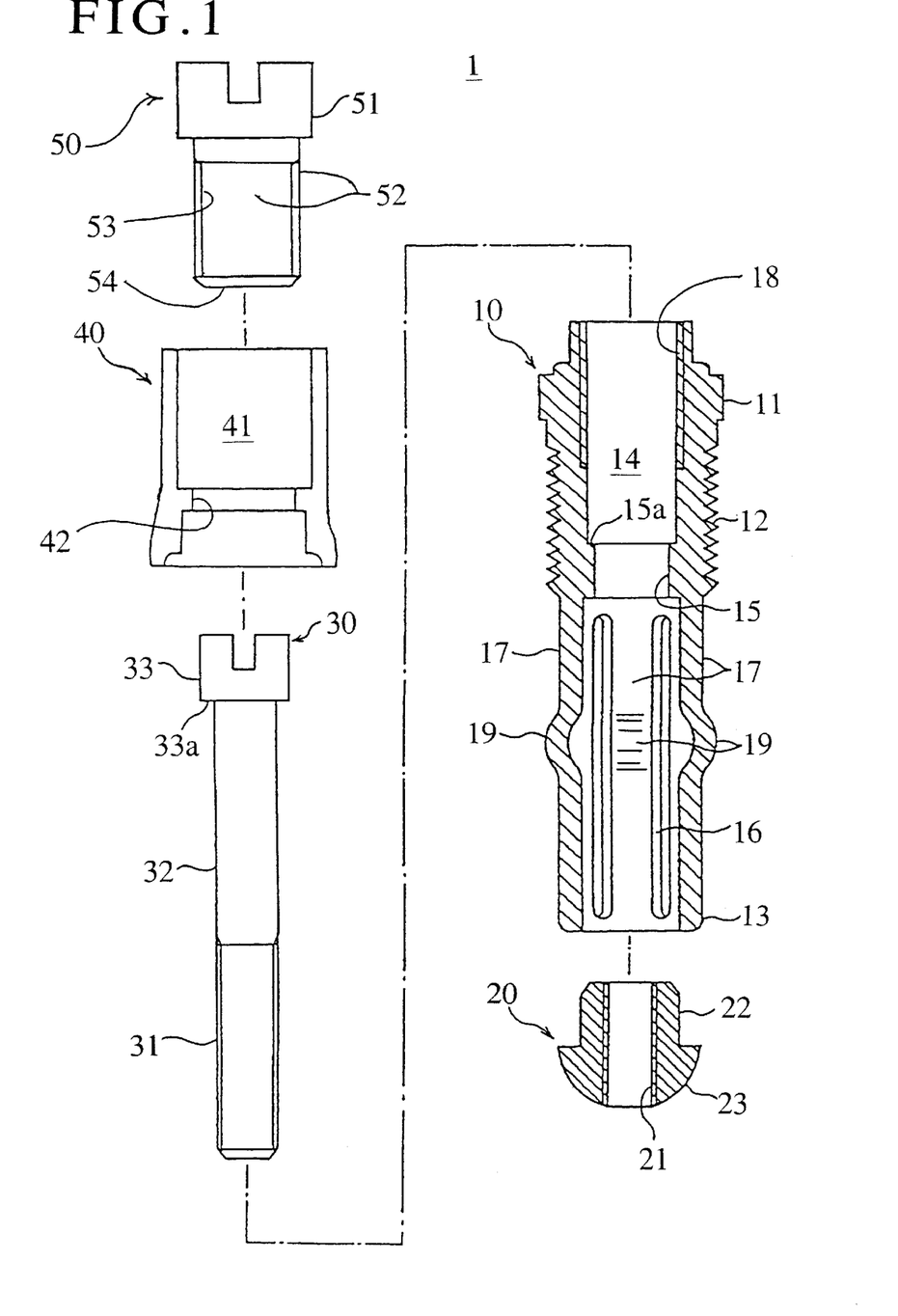
FIG. 1 is a decomposed sectional view showing the first preferred embodiment of the dental implant of the present invention.

FIG. 1 shows the dental implant 1 according to the first preferred embodiment of the present invention. This dental implant comprises a cylindrical body 10 called a fixture, a nut body 20, a first bolt body 30, a connecting body 40, and a second bolt body 50.

Figure 3A:
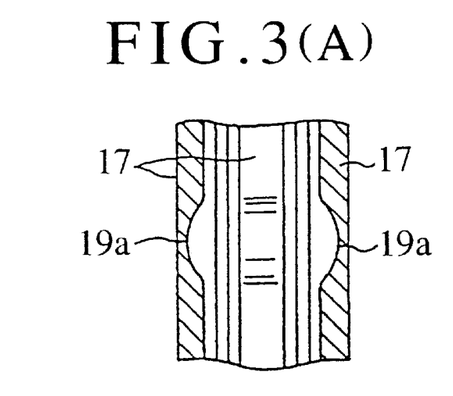
FIG. 3(A) is a partial sectional view of a modified example of the dental implant shown in FIG. 1.
Figure 3B:
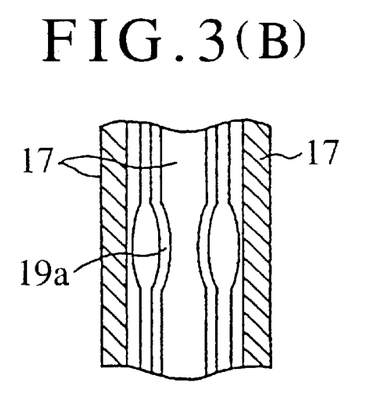
FIG. 3(B) is a partial sectional view of another modified example of the dental implant shown in FIG. 1.

The fixture 10 is composed of a titanium-alloy and has external male threads 12 near the head 11. In addition, the fixture 10 includes a circular internal shoulder 15 near the head 11 in the internal channel 14 passing through from the head 11 to a lower end (circular edge) 13. Further, the fixture 10 includes plural blade-like portions (skirt portion) 17 formed by cutting in plural slits from the internal shoulder 15 to the point 13 with a circular edge 13 left at the end of the fixture 10. In the middle of each blade-like portion 17, an outward bulge 19 is formed. Instead of the outward bulge 19, an inner concave dent 19a as shown in FIG. 3(A) or a narrowed portion 19b as shown in FIG. 3(B) may be formed. Further, female threads 18 are formed on the internal surface of upper portion of the fixture 10.

The nut body 20 is composed of a titanium-alloy, and has internal female threads 21. This nut body 20 includes a cylindrical portion 22 which has an external diameter slightly larger than the internal diameter of the end 13 of the fixture 10 and is pressed into the end 13 of the fixture 10, and includes a head 23 having a maximum diameter approximately equal to the external diameter of the end 13 of the fixture 10.

The first bolt body 30 is composed of a titanium-alloy. It includes a thread portion 32 having male threads 31, which are engaged with the female threads 21 of the nut body 20, and includes a head 33. The head 33 of the first bolt body 30 has an external diameter larger than the inner diameter of the internal shoulder 15 of the fixture 10. This first bolt body 30 is inserted into the internal channel 14 of the fixture 10 from the head 11, and its male threads 31 are engaged with the female threads 21.

The connecting body (abutment) 40 is composed of a titanium-alloy, and includes an internal channel 41 from the upper end to the under end. In addition, the connecting body 40 has an internal shoulder 42 near the under end. The inner diameter of the internal channel 41 under the internal shoulder 42 is smaller than the outer diameter of the head of the fixture 10 and larger than the inner diameter of the internal channel 14 of the fixture 10. The head of the fixture 10 slides into the under end of the internal channel 41 of the connecting body 40. Further, the upper portion of the connecting body 40 is embodied with a prosthesis.

The second bolt body (abutment screw) 50 is composed of a titanium-alloy. It includes a head 51, the diameter of which is larger than the inner diameter of the internal shoulder 42 of the connecting body 40 and smaller than the inner diameter of the portion of the internal channel 41 above the internal shoulder 42 of the connecting body 40, and includes a shank (thread portion) 52 having external male threads 53, the outer diameter of which is smaller than the inner diameter of internal shoulder 42 of the connecting body 40. Further, the male threads 53 of the second bolt body 50 are engaged with the female threads 18 on the internal surface of upper portion of the fixture 10.

Figure 2A:
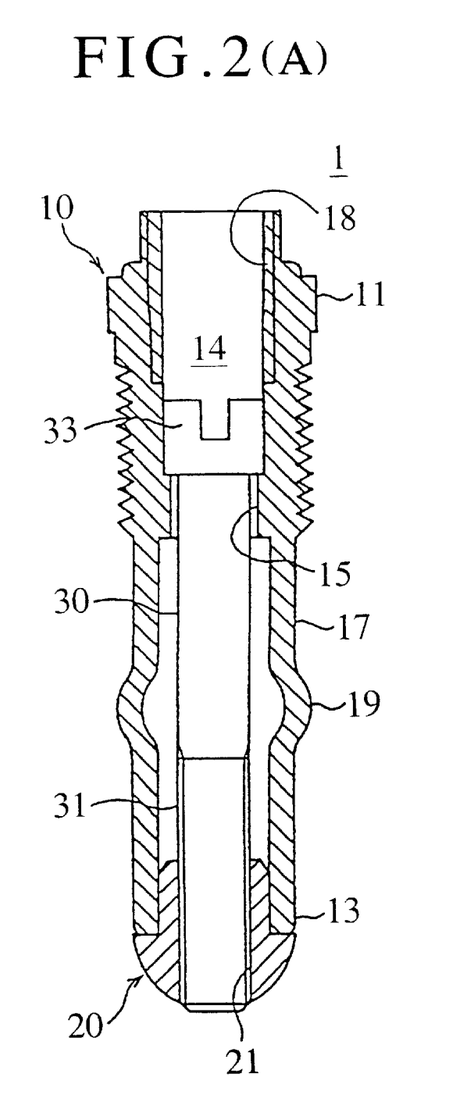
FIG. 2(A) is a sectional view of the dental implant shown in FIG. 1 before swelling the blade-like portions of the fixture.

The dental implant 1 of the construction described above, as shown in FIG. 2(A), is assembled by pressing the nut body 20 into the circular edge 13 of the fixture 10, inserting the first bolt body 30 in the internal channel 14 of the fixture 10 and engaging the male threads 31 thereof with the female threads 21 of the nut body, followed by equipping with the connecting body 40 and the second bolt body 50. After implanting the dental implant 1 within a bore of patient's jawbone, a rotating force (a torque) is applied on the head 33 of the first bolt body 30 by means of a proper tool such as a screw driver.

Figure 2B:
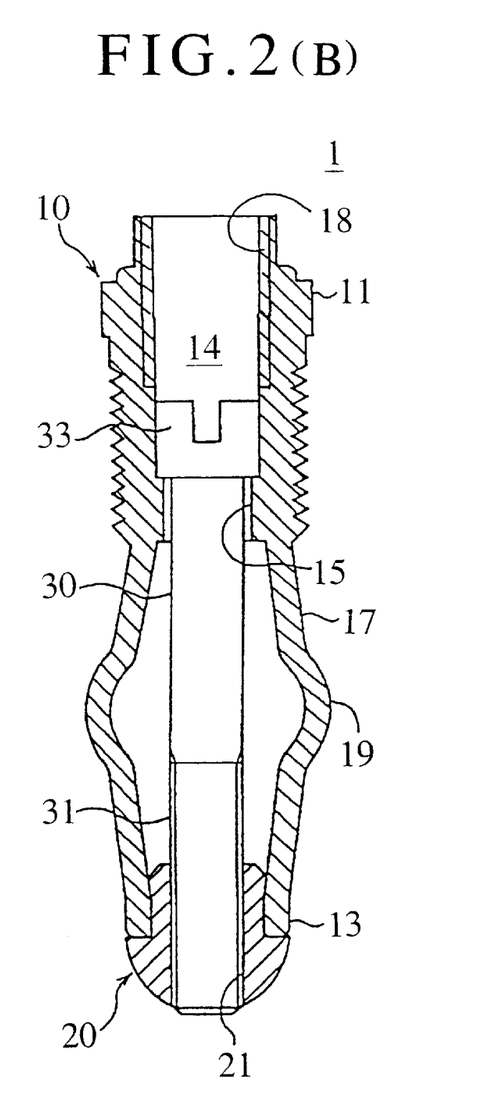
FIG. 2(B) is a sectional view of the dental implant shown in FIG. 1 after swelling the blade-like portions of the fixture into a spindle-like shape.

As described above, the internal shoulder 15 is provided in the internal channel 14 of the fixture 10, and the head 33 of the first bolt body 30 has the outer diameter larger than the inner diameter of the internal shoulder 15. Thus, the internal shoulder 15 plays the role of a stopper to prevent the downward motion of the head 33 of the first bolt body 30. Therefore, when a rotating force (a torque) is applied on the head 33 of the first bolt body 30 for allowing the nut body 20 to come near the head 33 of the first bolt body 30, the rotating force is converted to a force drawing up the circular edge 13 of the fixture 10 through the nut body 20, because the head 33 of the first bolt body 30 does not move downwards. Hence, a compressive force in the axis direction of the fixture 10 is applied on the blade-like portions 17, the both ends of which are fixed, so that as shown in FIG. 2(B), the blade-like portions 17 swell into a spindle-like shape, curving around the outward bulge 19, the concave dent 19a (FIG. 3(A)) or the convex jut 19b (FIG. 3(B)). As a result, the dental implant 1 is fixed within the bore of jawbone, compressing peripheral bone with the swelled blade-like portions 17.

When the blade-like portions 17 swell into a spindle-like shape and compress bone, the compressive force acts at the abdominal region of the blade-like portions 17 and then stresses are not concentrated. Therefore, the damaging effect due to stress concentration caused in the prior art by the points of blade-like portions (legs) deeply cutting into bone can be avoided. In addition, since the ends of the plural blade-like portions 17 are fixed by the circular edge 13 of the fixture 10 and the nut body 20 and since the blade-like portions 17 constitute a firm spindle-shaped structure, the breakdown of the blade-like portions 17 by twisting force can be avoided. Further, since the spindle-shaped structure is held firmly in bone as one body, horizontal micomotion also can be avoided.

Figure 4A:
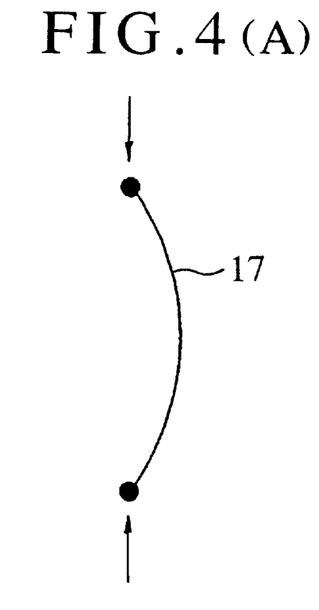
FIG. 4 is a mechanical model showing the force conditions applied to the blade-like portions of the dental implant of the present invention (A) and that of the prior art (B).
Figure 4B:
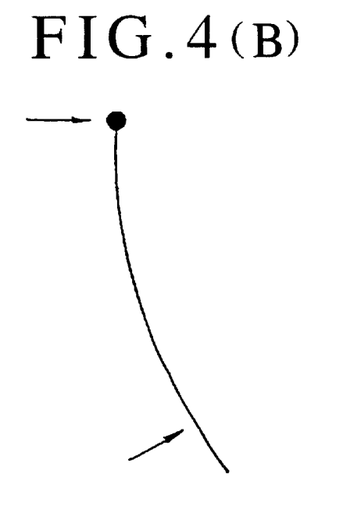

In the prior art, as shown in FIG. 4(B), one end (marked ●) of the blade-like portion (leg) is fixed, and the force is applied in the direction to expand the other end, almost perpendicularly to the chord of blade-like portion deformed into a bow-like shape. On the other hand, in the present invention, as shown in FIG. 4(A), the both ends (marked ●) of the blade-like portion 17 are fixed, and a compressive force is applied on the blade-like portion 17 in the direction almost parallel to the chord of blade-like portion 17 deformed into a bow-like shape. Hence, during the functioning of the dental implant such as mastication, when the same occlusal forces are applied downwards on the exposed head of the dental implant in the oral cavity, the amount of relative move of the head 33 of the bolt body 30 against the fixture 10 is far smaller in the present invention than in the prior art. Therefore, the possibility that the base 33a of the head 33 of the bolt body 30 and the upper surface 15a of the internal shoulder 15 of the fixture 10 are set apart from each other is far smaller, so that the superior preventive effect against the micro-leakage of bacteria to that of the prior art can be expected.

The Second Preferred Embodiment

Figure 5:
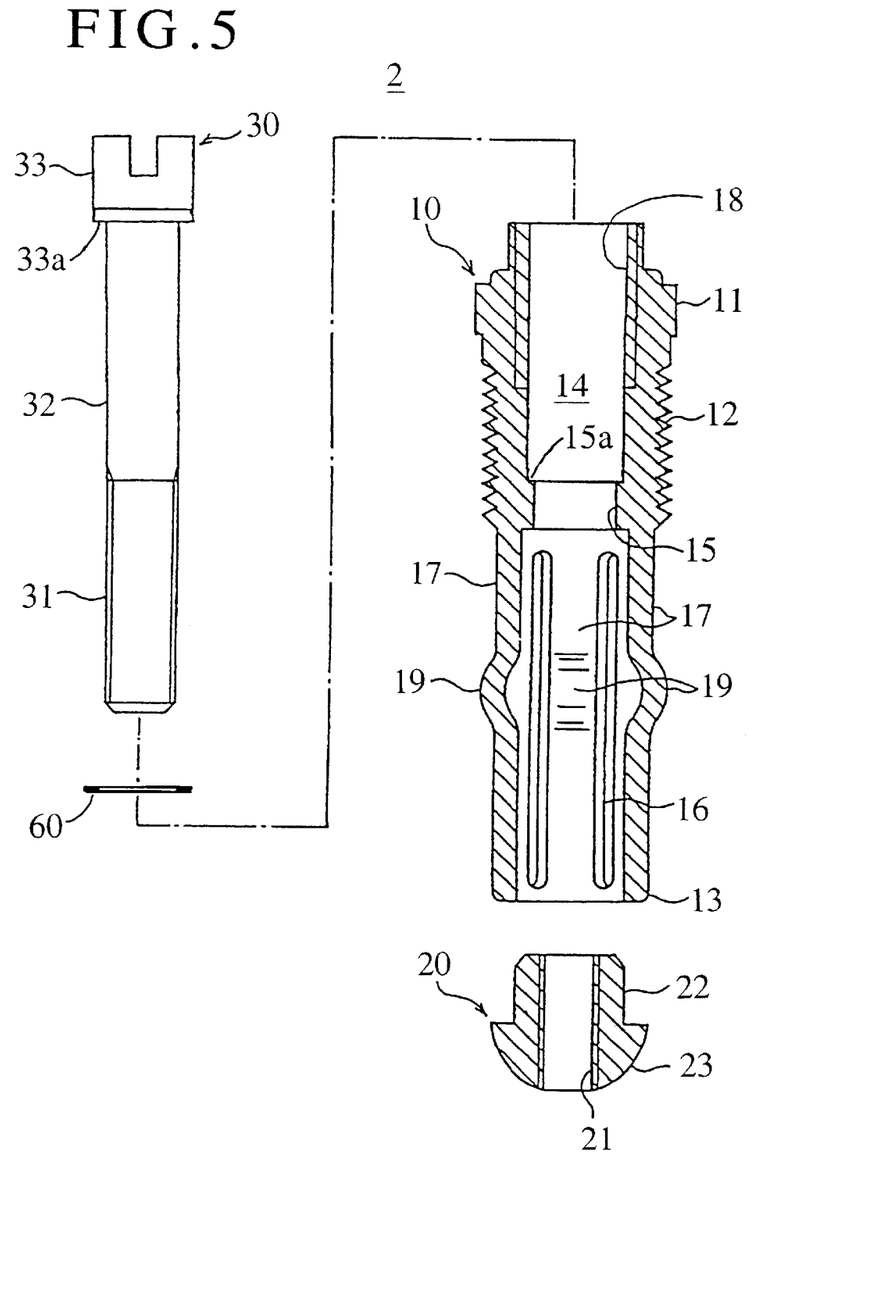
FIG. 5 is a decomposed sectional view showing the second preferred embodiment of the dental implant of the present invention.

FIG. 5 shows the dental implant 2 according to the second preferred embodiment of the present invention. In this implant 2 of the second preferred embodiment, a circular washer 60 composed of a metal softer than the first bolt body 30 or the fixture 10, for example, pure titanium is inserted between the head 33 of the bolt body 30 and the internal shoulder 15 of the fixture 10.

When the first bolt body 30 is firmly tightened to produce swelling of the plural blade-like portions 17 of the fixture 10 into a spindle-like shape, the circular washer 60 is compressed in close contact between the upper surface 15a of the internal shoulder 15 of the fixture 10 and the under surface 33a of the head 33 of the first bolt body 30 and deformed by strong compressive force, thereby causing a cold welding effect. Therefore, the passway for micro-leakage of bacteria is effectively sealed with the result that the effect to prevent microorganisms is reinforced.

The Third Preferred Embodiment

Figure 6:
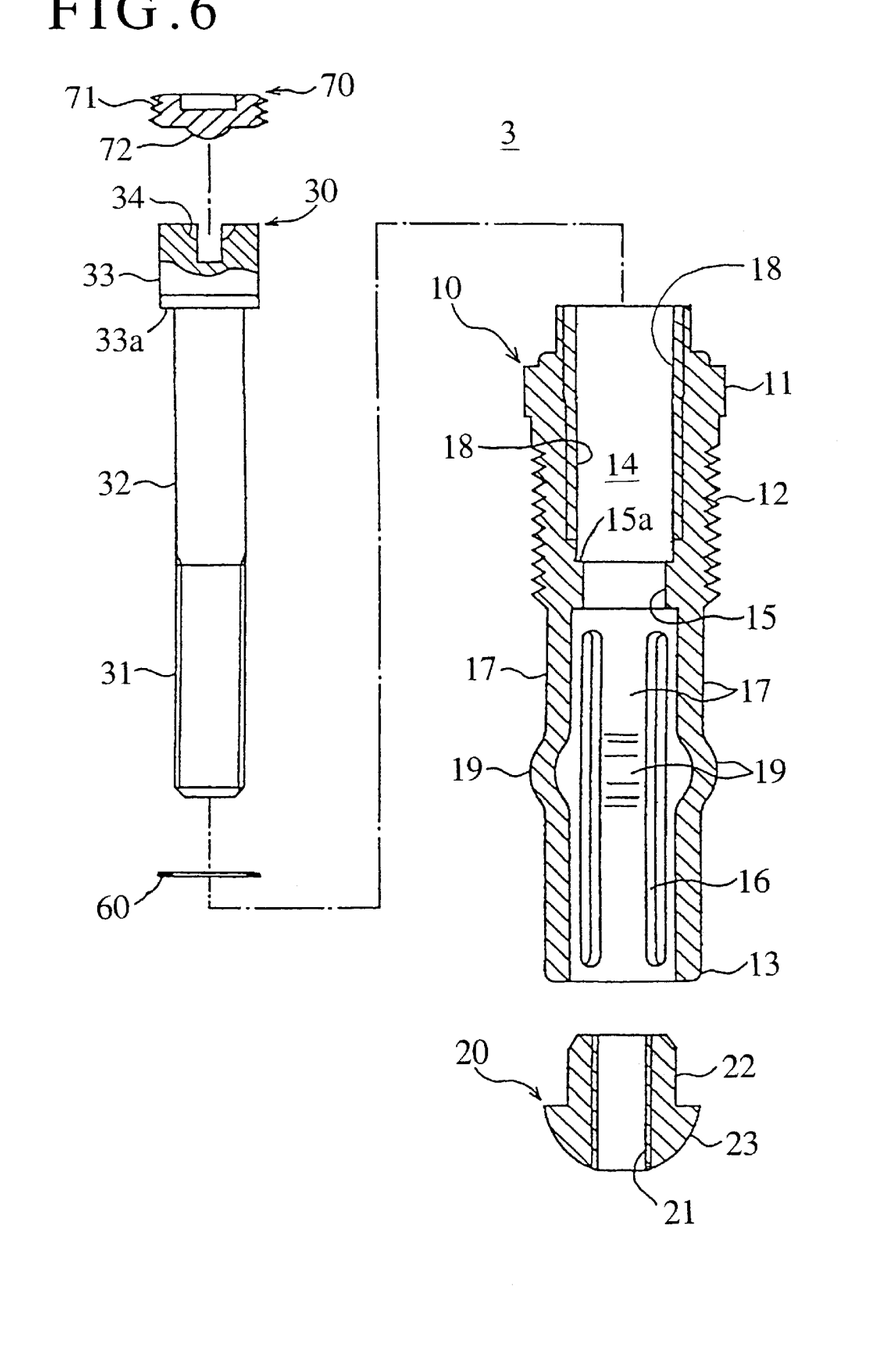
FIG. 6 is a decomposed sectional view showing the third preferred embodiment of the dental implant of the present invention.

FIG. 6 shows the dental implant 3 according to the third preferred embodiment of the present invention. In this dental implant of the third preferred embodiment, a threaded body 70 is added to the dental implant 2 of the second preferred embodiment. The threaded body 70 has male threads 71 on its outer surface and a convex jut 72 on its lower surface. On the other hand, on the inner surface of the internal channel 14 of the fixture 10 closer to the head 11 than the internal shoulder 15, female threads 19 with which the male threads 71 of the threaded body 70 are engaged are formed. Further, on the upper surface of the head 33 of the first bolt body 30, a concave dent 34 which fits closely to the convex jut 72 of the threaded body 70 is formed.

Hence, when strong compressive force is applied downwards on the head 33 of the first bolt body 30 by tightening the threaded body 70, the contact pressure between the under surface 33a of the head 33 of the first bolt body 30 and the upper surface 15a of the internal shoulder 15 of the fixture 10 increases with the result that the degree of close contact is enhanced and the preventive effect against microleakage of bacteria is reinforced.

The Fourth Preferred Embodiment

Figure 7:
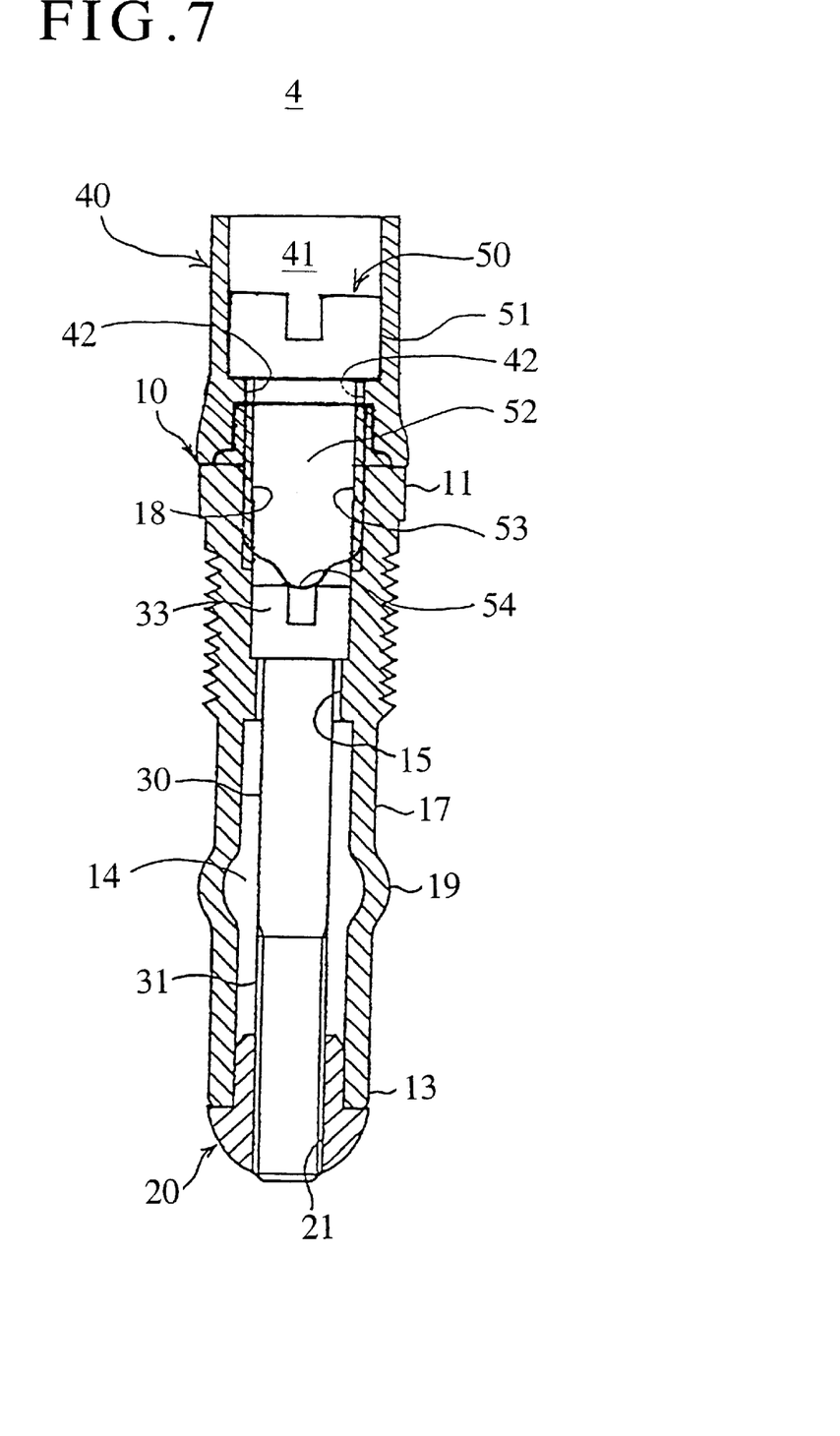
FIG. 7 is a decomposed sectional view showing the fourth preferred embodiment of the dental implant of the present invention.

FIG. 7 shows the dental implant 4 according to the fourth preferred embodiment of the present invention. In this dental implant of the fourth preferred embodiment, the role of the threaded body 70 of the third preferred embodiment is replaced by the second bolt body 50. The end 54 of the shank 52 of the second bolt body 50 is roundly pointed, and the shank 52 is lengthened until the end 54 of the shank 52 reaches and strongly presses the upper surface of the head 33 of the first bolt body 30 when the second bolt body 50 is rotated tightly while engaging the male threads 53 with the female threads 18 on the internal surface of the fixture 10. Thus, a close contact is realized between the under surface of the head 51 of the second bolt body 50 and the upper surface of the internal shoulder 42 of the connecting body 40. By strongly tightening the second bolt body 50, the compressive force between the upper surface 15a of the internal shoulder 15 of the fixture 10 and the under surface 33a of the head 33 of the first bolt body 30 is reinforced, through the circular washer 60 if it is present. Thus, the contact thereof is more close and the contact area is increased so that the passway of bacteria is more effectively sealed to thereby reinforce the preventive effect against microorganisms. This fourth preferred emodiment is advantageous in reducing the number of parts by one as well as the number of processes, because the circular washer 60 of the third preferred embodiment can be omitted.

In the above fourth preferred embodiment, the end 54 of the shank 52 of the second bolt body 50 may be composed of a metal softer than the first bolt body 30 or other part of the second bolt body 50. This strengthens the compressive force between the upper surface 15a of the internal shoulder 15 of the fixture 10 and the under surface 33a of the head 33 of the bolt body 30, when strongly tightening the second bolt body 50. Thus, the passway of bacteria is more effectively sealed so as to reinforce the preventive effect against microorganisms. It is preferable to use, for example, pure titanium as the metal of the end 54 of the shank 52 of the second bolt body 50.

In the preferred embodiments described hereinbefore, the internal shoulder 15 formed in the internal channel 14 of the fixture 10 plays the role of the stopper to prevent the downward movement of the head 33 of the first bolt body 30. Hence, when the first bolt body 30 is rotated while engaging it with the nut body 20, the head 33 of the first bolt body 30 does not move relative to the fixture 10, the nut body 20 is drawn upwards, and the blade-like portions (skirt portion) 17 are swelled into a spindle-like shape. However, the blade-like portions can be swelled by using a method other than the above preferred embodiments.

Such a method is shown in FIG. 8. In FIG. 8(A), the dental implant 5 is composed of a fixture 80, a semi-spherical body 90 and a screw body 100.

Figure 8A:
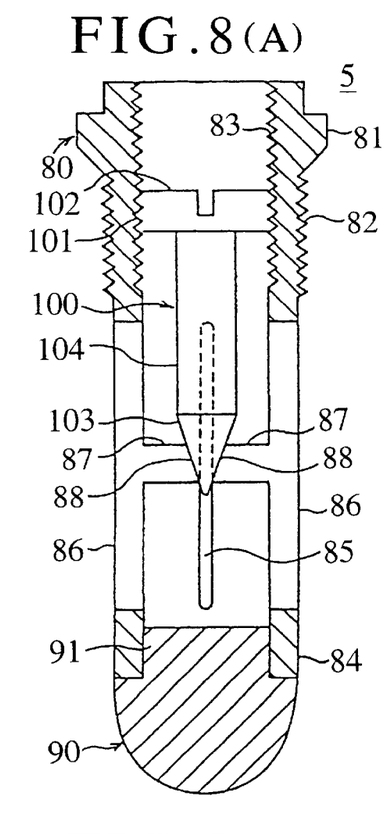
FIG. 8 is a decomposed sectional view showing a possibility of using a method other than the preferred embodiments of the dental implant of the present invention.
Figure 8B:
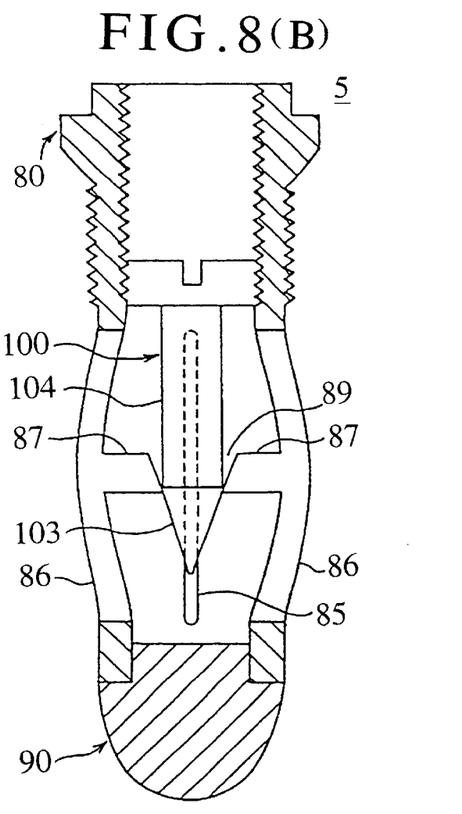
Figure 8C:
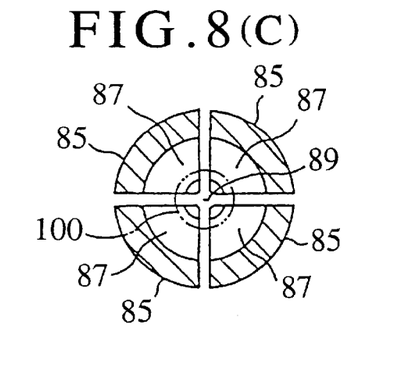
Figure 8D:
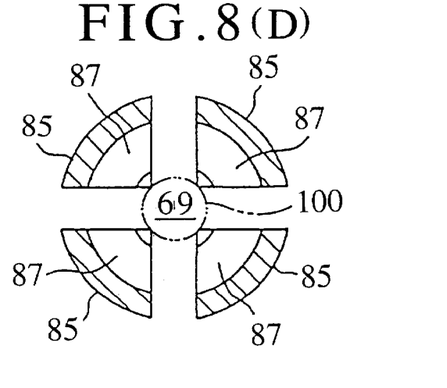

The fixture 80 is a cylindrical body composed of a titanium-alloy. Male threads 82 and female threads 83 are provided near the head 81 on its outer and inner surfaces, respectively. In addition, from the nearly middle to the point 84 of the fixture 80, plural slits 85 are cut in longitudinally, forming plural blade-like portions 86. Further, as shown in FIG. 8(C), sector-shaped internal shoulders 87 are provided on the middle of the inner surface of each blade-like portion 86, and reversed surfaces 88 are formed in the center of the sector-shaped internal shoulders 87. These reversed surfaces 88 form a central hole 89 of the internal shoulders 87.

The screw body 100 composed of a titanium-alloy includes a head 102 having outer male threads 101 which are engaged with the female threads 83 of the fixture 80 and a shank 104 having a point on which a bevel surface 103 is formed. When the screw body 100 is engaged through the head 81 of the fixture 80, the bevel surface 103 is slided in contact with the reversed bevel surface 88 of the internal shoulder 87 of the fixture 80.

In the dental implant 5 shown in FIG. 8, when the screw body 100 is moved downwards with the rotation of the screw body 100, the bevel 103 of the shank 104 of the screw body 100 is pushed into the central hole 89 of the internal shoulders 87 of the fixture 80. Hence, as shown in FIG. 8(B) and (D), plural blade-like portions 86 of the fixture 80 can be swelled into a spindle-like shape, exerting effects similar to those of the above preferred embodiments of the present invention.

EFFECT OF THE INVENTION

As apparent from the foregoing, in the use of the dental implant of the present invention, the ends of the plural blade-like portions of the cylindrical body (fixture) are fixed by the nut body, and the plural blade-like portions constitute a firm spindle-shaped structure as one body. Thus, the possibility that the blade-like portions are twisted or broke down can be avoided. Further, since the spindle-shaped structure is held firmly within a bore of a jawbone, horizontal micromotion can also be prevented.

In addition, the reactive force against the compressive force acting in the direction to shorten the length of the spindle-shaped structure is very strong. Therefore, during the functioning of the dental implant such as mastication, even when a strong downward occlusal force is applied on the exposed head of the implant in oral cavity, the possibility that the under surface of the head of the bolt body and the upper surface of the internal shoulder of the cylindrical body lose contact and are set apart from each other is far lower in the present invention than in the prior art. Consequently, the micro-leakage of bacteria can be prevented nearly to perfection.

As a result, the secure operation of the immediate loading of the dental implant, the realization of which has been the largest issue in modern dental implant, is attained and the operation period, for which three to six months have been required in the prior art, can be shortened within one day.

Although particular embodiments of the invention have been described in detail for purposes of illustration, various modifications may be made without departing from the spirit and scope of the invention. Accordingly, the invention is not limited, except as by the appended claims.

What is claimed is:

1. A dental implant comprising:
a cylindrical body receivable within a bore provided in a jawbone of a patient and having an internal channel from an upper end to an under end of the cylindrical body, including an annular internal shoulder at an upper middle of said internal channel and a skirt portion on an under half of the cylindrical body, plural slits being cut in on said skirt portion so as to form plural blade-like portions in the axis direction of said cylindrical body, female threads being formed on an internal surface of upper portion of said cylindrical body, a nut body including a cylindrical portion inserted into a circular edge of said skirt portion of said cylindrical body and an inner cavity having female threads, a first bolt body including on its upper end a head whose outer diameter is larger than an inner diameter of said internal shoulder of said cylindrical body and including on its under side a shank whose outer diameter is smaller than the inner diameter of said internal shoulder of said cylindrical body, said shank having male threads externally and being engaged with said female threads of said nut body, a connecting body having an internal channel from an upper end to an under end of the connecting body, including an internal shoulder near the under end of said connecting body, said connecting body having an inner diameter smaller than an outer diameter of head of said cylindrical body and larger than an inner diameter of said internal channel of said cylindrical body, the head of said cylindrical body being slided into an under end of said internal channel of said connecting body, head of said connecting body being embodied with a prosthesis, and a second bolt body including a head whose diameter is larger than an inner diameter of said internal shoulder of said connecting body and smaller than an inner diameter of portion of said internal channel of said connecting body positioned above said internal shoulder of said connecting body, and including a shank having male threads externally and having an outer diameter which is smaller than the inner diameter of said internal shoulder of said connecting body, said male threads of said second bolt body being engaged with said female threads provided on the internal surface of upper portion of said cylindrical body, so that inserting said first bolt body into the internal channel of said cylindrical body through said internal shoulder of said cylindrical body and rotating said first bolt body while engaging the male threads of the shank of said first bolt body with the female threads of said nut body causes swelling of said skirt portion of said cylindrical body into a spindle-like shape and causes close contact between a lower surface of the head of said first bolt body and an upper surface of said internal shoulder of said cylindrical body, and so that inserting said second bolt body into the internal channel of said connecting body through said internal shoulder of said connecting body, rotating said second bolt body while engaging the male threads of the shank of said second bolt body with the female threads of said internal channel of said cylindrical body and producing close contact between an under surface of the head of said second bolt body and an upper surface of said internal shoulder of said connecting body causes embodiment of said cylindrical body with a prosthesis through said connecting body.

2. The dental implant as set forth in claim 1, wherein said nut body is furnished with a head having an outer diameter larger than that of its cylindrical portion, said nut body having a maximum diameter substantially equal to an outer diameter of said skirt portion of said cylindrical body, and wherein the outer diameter of said cylindrical portion of said nut body is slightly larger than an inner diameter of said skirt portion of said cylindrical body, so that said cylindrical portion of said nut body can be pressed into a cavity of said skirt portion of said cylindrical body to thereby enable an immobilization.

3. The dental implant as set forth in claim 1, wherein an outward bulge is formed in the middle of each of said blade-like portions on said skirt portion of said cylindrical body.

4. The dental implant as set forth in claim 1, wherein a concave dent is internally formed in the middle of each of said blade-like portions on said skirt portion of said cylindrical body.

5. The dental implant as set forth in claim 1, wherein each of said blade-like portions on said skirt portion of said cylindrical body has its width narrowed in part in the middle thereof.

6. The dental implant as set forth in any of claims 1 to 5, wherein a circular washer composed of a metal softer than said cylindrical body or said first bolt body is interposed between the upper surface of said internal shoulder of said cylindrical body and the lower surface of the head of said first bolt body.

7. The dental implant as set forth in any of claims 1 to 5, wherein an additional threaded body having male threads on its external surface is engaged with the female threads provided on the internal surface of upper portion of said cylindrical body, said additional threaded body having a convex just on its under surface, said head of said first bolt body having its upper surface furnished with a concave dent which fits closely with said convex jut.

8. The dental implant as set forth in any of claims 1 to 5, wherein a lower end of said shank of said second bolt body is roundly pointed, and wherein said lower end of said shank is adapted to reach and press an upper surface of the head of said first bolt body when said second bolt body is rotated while engaging the male threads of the shank of said second bolt body with the female threads of said internal channel of said cylindrical body, so that a close contact is realized between an under surface of the head of said second bolt body and an upper surface of said internal shoulder of said connecting body.

9. The dental implant as set forth in claim 8, wherein the lower end of said shank of said second bolt body is composed of a metal softer than said first bolt body or other part of said second bolt body.

* * * * *